United States Patent [19]

Abe et al.

[11] Patent Number: 4,774,013

[45] Date of Patent: Sep. 27, 1988

[54] PERHYDROFLUORENE DERIVATIVES AND FLUIDS FOR TRACTION DRIVE

[75] Inventors: Kazuaki Abe; Toshiyuki Tsubouchi; Hitoshi Hata, all of Sodegaura, Japan

[73] Assignee: Idemitsu Kosan Company Limited, Tokyo, Japan

[21] Appl. No.: 126,078

[22] Filed: Nov. 24, 1987

[30] Foreign Application Priority Data

Nov. 25, 1986 [JP] Japan .............................. 61-280096

[51] Int. Cl.$^4$ ................. C10M 105/04; C10M 127/02
[52] U.S. Cl. ........................................ 252/73; 585/22;
585/254; 585/267; 585/268
[58] Field of Search ................... 252/73; 585/22, 254,
585/267, 268

[56] References Cited

U.S. PATENT DOCUMENTS

3,411,369  11/1968  Hammann et al. ..................... 585/2
3,843,537  10/1974  Duling et al. ........................... 585/10

*Primary Examiner*—Robert Wax
*Attorney, Agent, or Firm*—Armstrong, Nikaido, Marmelstein & Kubovcik

[57] ABSTRACT

This invention provides a novel perhydrofluorene derivative which is represented by the following general formula and which is useful as a fluid for traction drive and a process for production of the derivative.

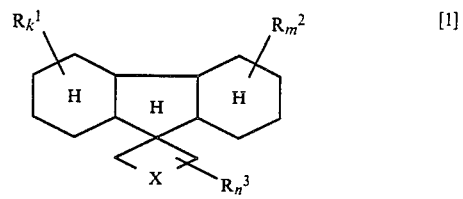

wherein $R^1$, $R^2$ and $R^3$ each represents a hydrogen atom or an alkyl group of 1-4 carbon atoms, X represents $(CH_2)_p$ or

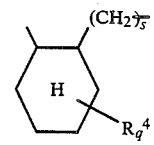

wherein $R^4$ represents a hydrogen atom or an alkyl group of 1-4 carbon atoms, p represents a real number of 2-6, q represents a real number of 1-4 and s represents 1 or 0 and k, m and n each represents a real number of 1-4.

6 Claims, 10 Drawing Sheets

PERHYDROFLUORENE DERIVATIVES AND FLUIDS FOR TRACTION DRIVE

BACKGROUND OF THE INVENTION

This invention relates to a perhydrofluorene derivative, a process for producing the same and fluid for traction drive which contains the same. More particularly, it relates to a perhydrofluorene drivative suitable as a fluid used for traction driving devices such as automatic transmission device in automobiles, variable-speed transmission devices of machines, etc., a process for efficiently producing said derivative by a simple operation and fluid for traction drive which make it possible to make traction driving devices smaller and lighter.

Recently, miniaturization and lightening of traction driving devices by using fluid have been studied especially in the field of automoboiles. Thus, development of traction driving fluids having high performances in a wide temperature range has been demanded.

That is, it is desired for fluid for traction drive that even if viscosity thereof increases at low temperatures, they can be practically used in a temperature range where they are normally used, for example, −30° C.–140° C. and further retain high traction coefficients at high temperatures and have high heat stability and oxidation stability.

Hitherto, for example, a perhydrofluorene compound represented by the following general formula:

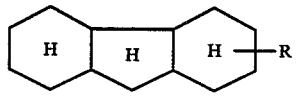

(wherein R represents a cyclohexyl group, an ethyl group or a lauryl group) has been proposed as traction driving fluid. [cf. Japanese Patent Publication (Kokoku) No. 338/71 corresponding to U.S. Pat. No. 3,411,369].

However, this perhydrofluorene compound is low in traction coefficient and so, contacting area of fluid and mechanical part must be increased when this compound is used as a traction driving fluid and this is disadvantageous for miniaturization of traction driving devices.

SUMMARY OF THE INVENTION

This invention has been made under the above circumstances.

The object of this invention is to provide a novel compound which has low viscosity and has high traction coefficient even at high temperatures and thus, can make traction driving devices smaller and lighter and a process for producing said compound and further fluid for traction drive containing said compound.

As a result of the inventors' intensive researches in an attempt to accomplish the above objects, it has been found that a specific perhydrofluorene compound has high traction coefficient even at high temperatures and besides is low in viscosity. Thus, this invention has been completed.

The summary of the first invention to accomplish the above objects and solve the above problems is a perhydrofluorene derivative represented by the following formula [1]:

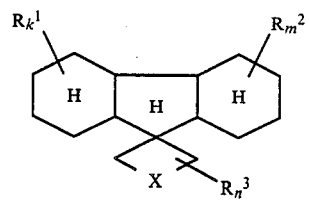

(wherein $R^1$, and $R^2$ and $R^3$ each represents a hydrogen atom or an alkyl group of 1–4 carbon atoms, X represents $(CH_2)_p$ or

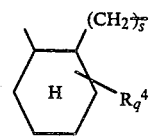

(where $R^4$ represents a hydrogen atom or an alkyl group of 1–4 carbon atoms, p represents a real number of 2–6, q represents a real number of 1–4 and s represents 1 or 0) and k, m and n each represents a real number of 1–4).

The summary of the second invention is a process for producing a perhydrofluorene derivative, characterized by contacting a fluorene derivative represented by the following formula [2]:

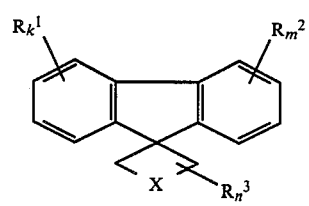

(wherein $R^1$, $R^2$ and $R^3$ each represents a hydrogen atom or an alkyl group of 1–4 carbon atoms, X represents $(CH_2)_p$ or

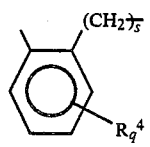

(wherein $R^4$ represents a hydrogen atom or an alkyl group of 1–4 carbon atoms, p represents a real number of 2–6, q represents a real number of 1–4 and s represents 1 or 0) and k, m and n each represents a real number of 1–4) with hydrogen in the presence of a hydrogenation catalyst.

The summary of the third invention is fluid for traction drive, characterized by containing the perhydrofluorene derivative represented by the above formula [1].

DESCRIPTION OF THE INVENTION

Figure 1:
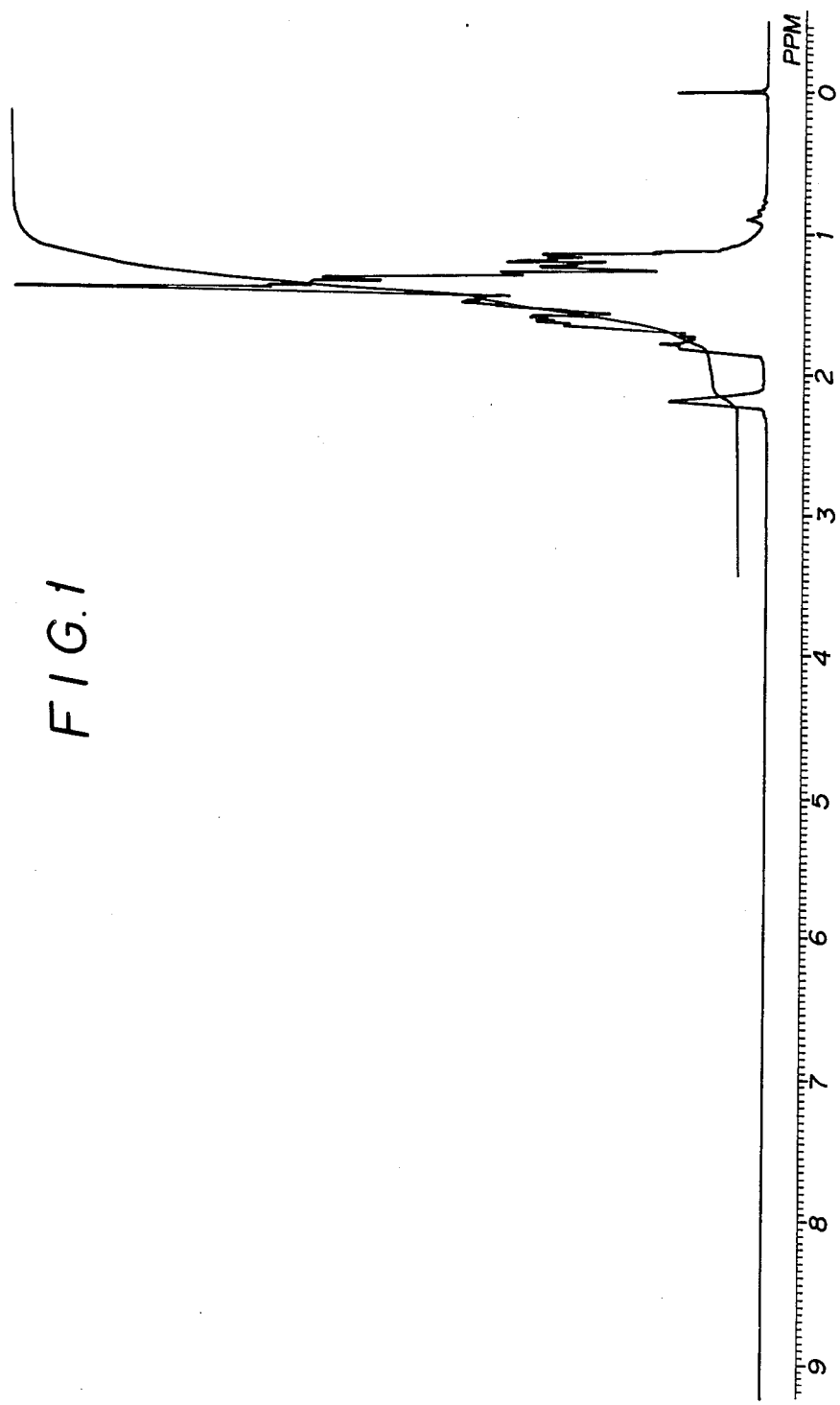
FIG. 1 is a spectral chart which shows the results of proton nuclear magnetic resonance spectral analysis of one example of the perhydrofluorene derivative of this invention.

The perhydrofluorene derivative of this invention is represented by the following formula [1]:

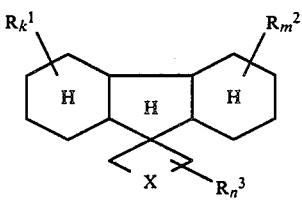

In the above formula [1], $R^1$, $R^2$ and $R^3$ each represents a hydrogen atom or an alkyl group of 1-4 carbon atoms, more specifically a hydrogen atom, a methyl group, an ethyl group, a propyl group or a butyl group, preferably hydrogen atom and methyl group and especially preferably hydrogen atom. $R^1$, $R^2$ and $R^3$ may be identical or different.

Examples of X in the formula [1] are as follows:

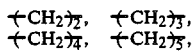

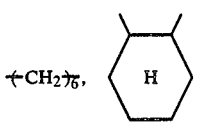

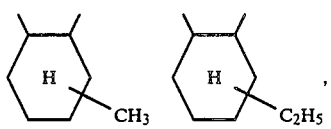

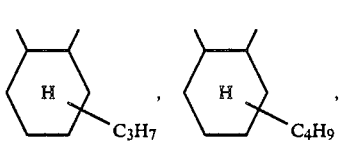

Among them, preferred at $-(CH_2)_3-$, $-(CH_2)-$ and

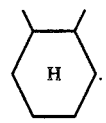

The perhydrofluorene derivative represented by the above formula [1] can be produced by contacting a fluorene derivative represented by the following formula [2]:

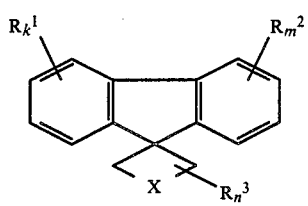

(wherein $R^1$, $R^2$ and $R^3$ each represents a hydrogen atom or an alkyl group of 1-4 carbon atoms, X represents $-(CH_2)_p-$ or

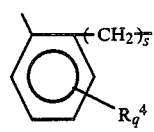

(wherein $R^4$ represents a hydrogen atom or an alkyl group of 1-4 carbon atoms, p represents a real number of 2-6, q represents a real number of 1-4 and s represents 1 or 0) and k, m and n each represents a real number of 1-4) with hydrogen in the presence of a hydrogenation catalyst.

The fluorene derivative represented by the formula [2] can be produced, for example, by reacting a fluorene derivative represented by the following formula [3]:

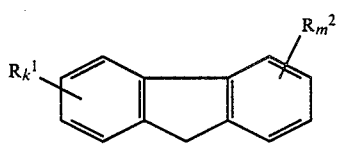

with a dihalogenated hydrocarbon as shown below.

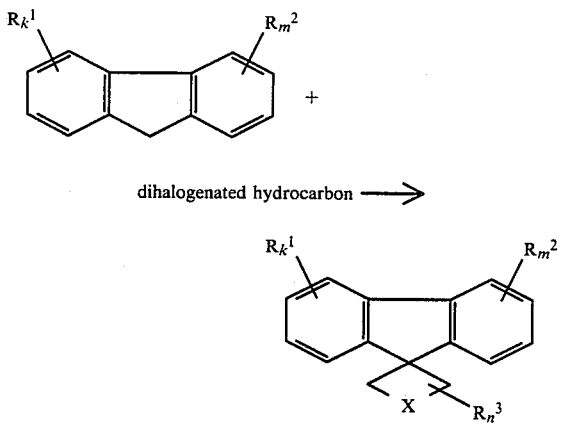

dihalogenated hydrocarbon ⟶

Reaction temperature of the above reaction is normally 0°–250° C. and reaction time is normally 10 minutes–30 hours.

The above reaction proceeds in the presence of a catalyst and as the catalyst, mention may be made of, for example, alkali metal hydroxides such as lithium hydroxide, sodium hydroxide, potassium hydroxide, rubidium hydroxide and cesium hydroxide; alkali metal carbonates such as sodium carbonate, potassium carbonate and lithium carbonate; alcoholates such as sodium alcoholate and potassium alcoholate; organic alkali metal compounds such as n-butyl lithium and amyl sodium; sodium amide, metallic sodium, metallic potassium, etc.

The above reaction is normally carried out in a solvent.

The solvent used depends on the kind of catalysts used.

For example, when the catalyst is an alkali metal hydroxide, solvent used can be one or more of aromatic hydrocarbons (e.g., benzene, toluene, xylene, etc.), aliphatic hydrocarbons (e.g., hexane, pentane, cyclohexane, decalin, etc.), methylene chloride, chloroform, water, etc.

When water is used as solvent, yield can be further increased by using a phase-transfer catalyst (e.g., tetrabutylammonium hydrogensulfite, triethylbenzylammonium chloride, etc.) as a promotor.

When the catalyst used is an alkali metal carbonate, the solvent can be one or more of ketones (e.g., acetone, methyl ethyl ketone, etc.), aromatic hydrocarbons (e.g., benzene, toluene, xylene, etc.), etc. When an alcoholate is used as catalyst, the solvent can be alcohols (e.g., methyl alcohol, ethyl alcohol, tert-butyl alcohol, etc.).

When the catalyst used is an organic alkali metal, sodium amide or the like, the solvent can be one or more of ethers (e.g., diethyl ether, tetrahydrofuran, dioxane, etc.), aliphatic hydrocarbons (e.g., hexane, cyclohexane, pentane, decalin, etc.), DMF, DMSO, etc.

When the catalyst is a metallic sodium, metallic potassium or the like, the solvent can be one or more of aromatic hydrocarbons (e.g., benzene, toluene, xylene, etc.), aliphatic hydrocarbons (e.g., hexane, cyclohexane, decalin, etc.), etc.

According to this invention, the perhydrofluorene derivative represented by the formula [1] is produced by contacting the fluorene derivative represented by the formula [2] obtained by said reaction, with hydrogen in the presence of a hydrogenation catalyst.

Hydrogen used has no special limitation as long as it can hydrogenate the fluorene derivative represented by the formula [2]. For example, there may be used hydrogen obtained by electrolysis of water, conversion of water gas, gasification of petroleums, conversion of natural gas, etc.

As the hydrogenation catalyst, there may be used those which are normally used for hydrogenation.

As examples of the catalyst, mention may be made of nickel cobalt catalysts such as nickel suflide, nickel peroxide, nickel-pumice catalyst, nickel-thoria-diatomaceous earth catalyst, nickel-copper-alumina catalyst, nickel-diatomaceous earth catalyst, nickel-alumina catalyst, nickel-beryllia catalyst, nickel-chromina catalyst, nickel-chromite catalyst, nickel calcium phosphate catalyst, Raney nickel catalyst, Urushibara nickel catalyst, nickel formate, cobalt-diatomaceous earth catalyst, cobalt-copper catalyst, cobalt-barium oxide-alumina catalyst, cobalt-molybdenum catalyst, cobalt-thoria diatomaceous earth catalyst, cobalt-thoria magnesia-diatomaceous earth catalyst, Raney cobalt catalyst, Urushibara cobalt catalyst, cobalt formate catalyst, etc.; platinum group catalysts such as ruthenium chloride, ammonium chlororuthenate, ruthenium hydroxide, ruthenium dioxide catalyst, potassium ruthenate, ruthenium hydroxide catalyst, ruthenium-carbon catalyst, supported ruthenium catalyst, colloidal rhodium catalyst, rhodium oxide catalyst, rhodium hydroxide catalyst, supported rhodium catalyst, rhodium chloride, sodium chlororhodinate, ammonium chlororhodinate, rhodium hydroxide, rhodium oxide, palladium chloride catalyst, chlorotetrammine palladium, ammonium tetrachloropalladate, palladium oxide, palladium hydroxide, palladium catalyst, palladium hydroxide catalyst, supported palladium catalyst, palladium hydroxide-carbon catalyst, palladium-barium sulfate catalyst, palladium-calcium carbonate catalyst, other supported catalysts, osmium black catalyst, colloidal osmium catalyst, osmium-carbon catalyst, osmium-alumina catalyst, iridium black catalyst, colloidal iridium catalyst, iridium oxide catalyst, iridium oxide-platinum oxide catalyst, iridium-asbestos catalyst, iridium-carbon catalyst, platinum black catalyst, colloidal platinum catalyst, platinum-carbon catalyst, platinum-asbestos catalyst, platinum-silica gel catalyst, platinum-alumina catalyst, etc. Among these catalysts, preferred are ruthenium catalysts such as ruthenium chloride, ammonium chlororuthenate, ruthenium hydroxide, ruthenium dioxide catalyst, potassium ruthenate, ruthenium hydroxide catalyst, ruthenium-carbon catalyst, supported ruthenium catalysts, etc.; rhodium catalysts such as colloidal rhodium catalyst, rhodium oxide catalyst, rhodium hydroxide catalyst, supported rhodium catalyst, rhodium chloride, sodium chlororhodinate, ammonium chlororhodinate, rhodium hydroxide, rhodium oxide, etc.; platinum catalysts such as platinum black catalyst, colloidal platinum catalyst, platinum-carbon catalyst, platinum-asbestos catalyst, platinum-silica gel catalyst, platinum-alumina catalyst, etc. and especially preferred is ruthenium-carbon catalyst.

Reaction temperature for the above reaction is usually room temperature–300° C., preferably 50°–200° C. and reaction pressure is usually 1–250 kg/cm²G, preferably 5–150 kg/cm²G.

When the reaction temperature is too low, sometimes the reaction does not sufficiently proceed and when higher than 300° C., activity of the catalyst sometimes reduces.

When the reaction pressure is outside said range, catalytic activity sometimes reduces.

Solvent can be used in the process for production of perhydrofluorene derivative of this invention.

Solvents used in the process may be those which can dissolve the fluorene derivative which is starting material. Examples of solvents are saturated hydrocarbon solvents (e.g., cyclohexane, methylcyclohexane, hexane, etc.), aromatic hydrocarbon solvents (e.g., toluene, xylene, benzene, etc.), ester solvents (e.g., methyl acetate, ethyl acetate, etc.), alcohol solvents (e.g., methyl alcohol, ethyl alcohol, etc.), ketone solvents (e.g., acetone, MEK, etc.), etc.

The fluid for traction drive of this invention contains the perhydrofluorene derivative represented by the formula [1], preferably its cis-isomer, but is may be used in admixture with other fluids for traction drive. Further, if necessary, the fluid of this invention may contain antioxidant, rust preventive, defoamer, viscosity index improver, pour point depressant, detergent-dispersant, extreme pressure additive, oiliness improver, etc.

The antioxidant includes, for example, aromatic amine compounds, phenolic compounds, zinc dialkyldithiophosphate compounds, phosphorus compounds, etc.

The rust preventative includes, for example, organic compounds having polar group such as sulfonates, amines, organic acids, their salts and esters, etc.

The defoamer includes, for example, organosilicone compound polymers such as polymethylsiloxane, etc.

The viscosity index improver includes, for example, isobutylene polymer, methacrylate polymer, etc.

The pour point depressant includes, for example, chlorinated paraffin naphthalene condensate, polymethacrylate, etc.

The fluid for traction drive of this invention contains the perhydrofluorene derivative represented by the formula [1] which shows less increase in viscosity at low temperatures and maintains high traction coefficient even at high temperatures and therefore it can be advantageously used for traction drive devices for automobiles which strongly demand miniaturization in size and lightening in weight.

Since the perhydrofluorene derivative of this invention is less in increase of viscosity at low temperatures and besides has high traction coefficient even at high temperatures, it is not only suitable as fluid for traction drive device, but also can be used as lubricating oil, heat transfer oil and electrical insulating oil.

Furthermore, the perhydrofluorene derivative of this invention is produced bycontacting a fluorene derivative with hydrogen in the presence of a hydrogenation catalyst. Thus, the perhydrofluorene derivative can be efficiently produced by a simple operation.

Further, since the fluid for traction drive of this invention contains the perhydrofluorene derivative which has high traction coefficient even at high temperatures, the contacting area of the fluid with mechanical parts can be decreased and as a result miniaturization and lightening of traction drive device can be attained.

Therefore, according to this invention, (1) a novel compound can be provided which is low in viscosity and has high traction coefficient even at high temperatures, (2) an industrially useful process can be provided which can produce the compound efficiently and by a simple operation and furthermore, (3) a novel fluid for traction drive can be provided which can attain miniaturization and lightening of traction drive devices.

This invention will be further illustrated by the following examples.

EXAMPLE 1

(1) Preparation of fluorene derivative:

300 ml of 50% aqueous sodium hydroxide solution, 170.5 g (1.03 mol) of fluorene, 5.61 g (0.025 mol) of triethylbenzylammonium chloride, 273 g (1.03 mol) of 1,5-dibromopentane and 6 ml of dimethylsulfoxide were charged in a four necked flask of 2 liters equipped with a thermometer, a Liebig condenser and stirrer and were stirred at 135° C. for 3 hours.

After discontinuation of stirring, 400 ml of toluene and 400 ml of water were added and the content was transferred to a separating funnel to separate aqueous layer. The organic layer was washed with 500 ml of water four times and then dried over anhydrous magnesium sulfate. Then, the drying agent was removed by filtration and toluene was distilled off by rotary evaporator. The residue was subjected to distillation under reduced pressure to obtain 115 g of a fraction having a boiling point of 160°–165° C. (0.1 mmHg). This fraction solidified in short time and was recrystallized twice from ethanol to obtain 110 g of a white crystal (melting point: 81.5°–81.8° C.). this compound was analyzed to find that this was spiro[cyclohexane-1,9'-fluorene] which contained spiro-union at 9-position of fluorene.

(2) Preparation of perhydrofluorene derivative:

110 g of spiro[cyclohexane-1,9'-fluorene] obtained in the above (1), 100 ml of cyclohexane solvent and 20 g of 5% ruthenium-carbon catalyst (manufactured by Japan Engelhard Co.) were charged in an autoclave of 1 liter and hydrogenation was effected with a hydrogen pressure of 80 kg/cm$^2$G at 170° C. for 5 hours.

After cooling, the catalyst was removed by filtration and cyclohexane was distilled off to obtain 110 g of a product. This product was subjected to proton nuclear magnetic resonance spectral analysis, $^{13}$C nuclear magnetic resonance spectral analysis and mass spectral analysis to find that hydrogenation rate was at least 99% and the product was perhydrospiro[cyclohexane-1,9'-fluorene] of purity 99% produced by nuclear hydrogenation of the starting spiro[cyclohexane-1,9'-fluorene] as such obtained in (1). The results are shown in Table 1.

Figure 2:
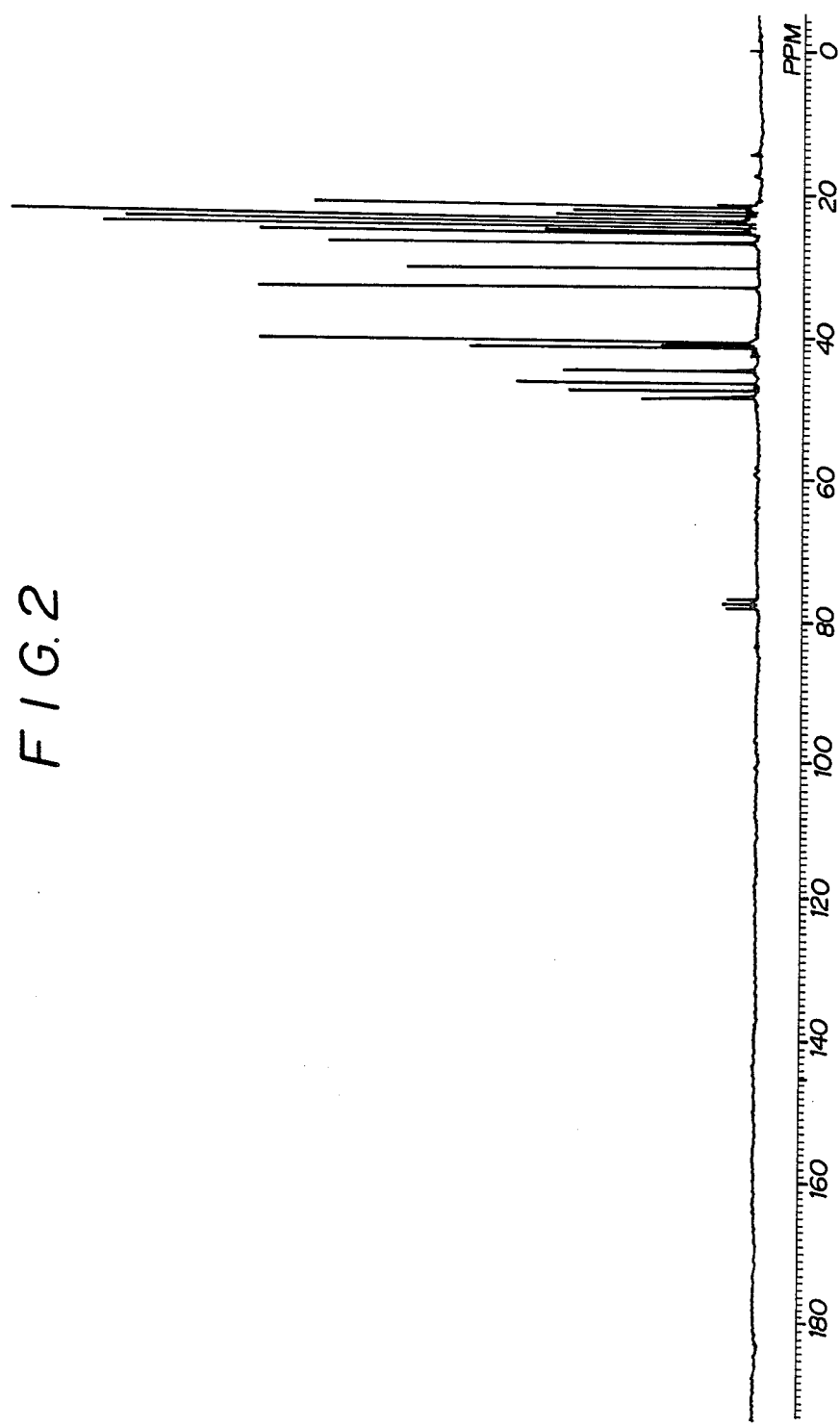
FIG. 2 is a spectral chart which shows the results of 13C nuclear magnetic rsonance spectral analysis of the derivative.
Figure 3:
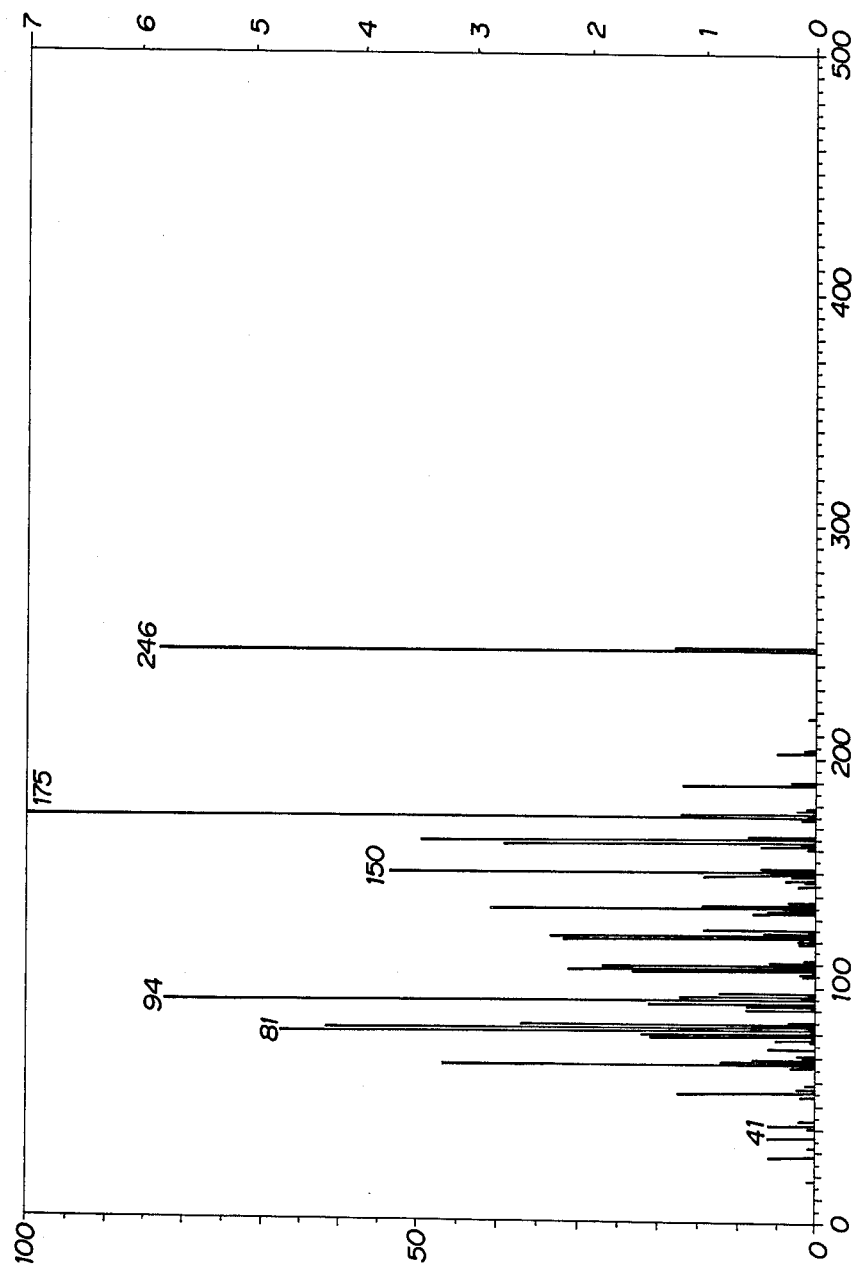
FIG. 3 is a spectral chart which shows the results of mass spectral analysis of the derivative.

The results of proton nuclear magnetic resonance spectral analysis are shown in FIG. 1, the results of $^{13}$C nuclear magnetic resonance spectral analysis are shown in FIG. 2 and the results of mass spectral analysis are shown in FIG. 3.

The purity was measured by FID gas chromatography, the proton nuclear magnetic resonance spectral analysis and $^{13}$C nuclear magnetic resonance spectral analysis were carried out by GX-270 nuclear magnetic resonance device manufactured by Nippon Denshi Co. and the mass spectral analysis was carried out by M-60 gas chromatograph mechanical spectrometer manufactured by Hitachi Ltd.

(3) Measurement of traction coefficient

Traction coefficient of perhydrospiro[cyclohexane-1,9'-fluorene] obtained in the above (2) was measured using two roller machine abrader having two rollers of a drum-shaped roller to be drived of 52 mm in diameter, 6 mm in thickness and 10 mm in crown radius and a flat type roller of 52 mm in diameter and 6 mm in thickness.

That is, one roller was rotated at a given speed (1500 rpm) and another was continuously rotated at from 1500 rpm to 1750 rpm and a load of 7 kg was applied to the contacting portion of the two rollers by a spring. Traction coefficient in the range of 40° C.–140° C. was obtained by measuring the tangential force (traction force) generated between the two rollers. These rollers were made of bearing steel SUJ-2 of mirror finish and maximum hertzian contacting pressure was 112 kg/mm². For measurement of relation between traction coefficient and oil bath temperature, oil temperature was changed from 40° C. to 140° C. by heating oil tank by a heater and the relation at slip ratio of 5% was obtained.

Figure 4:
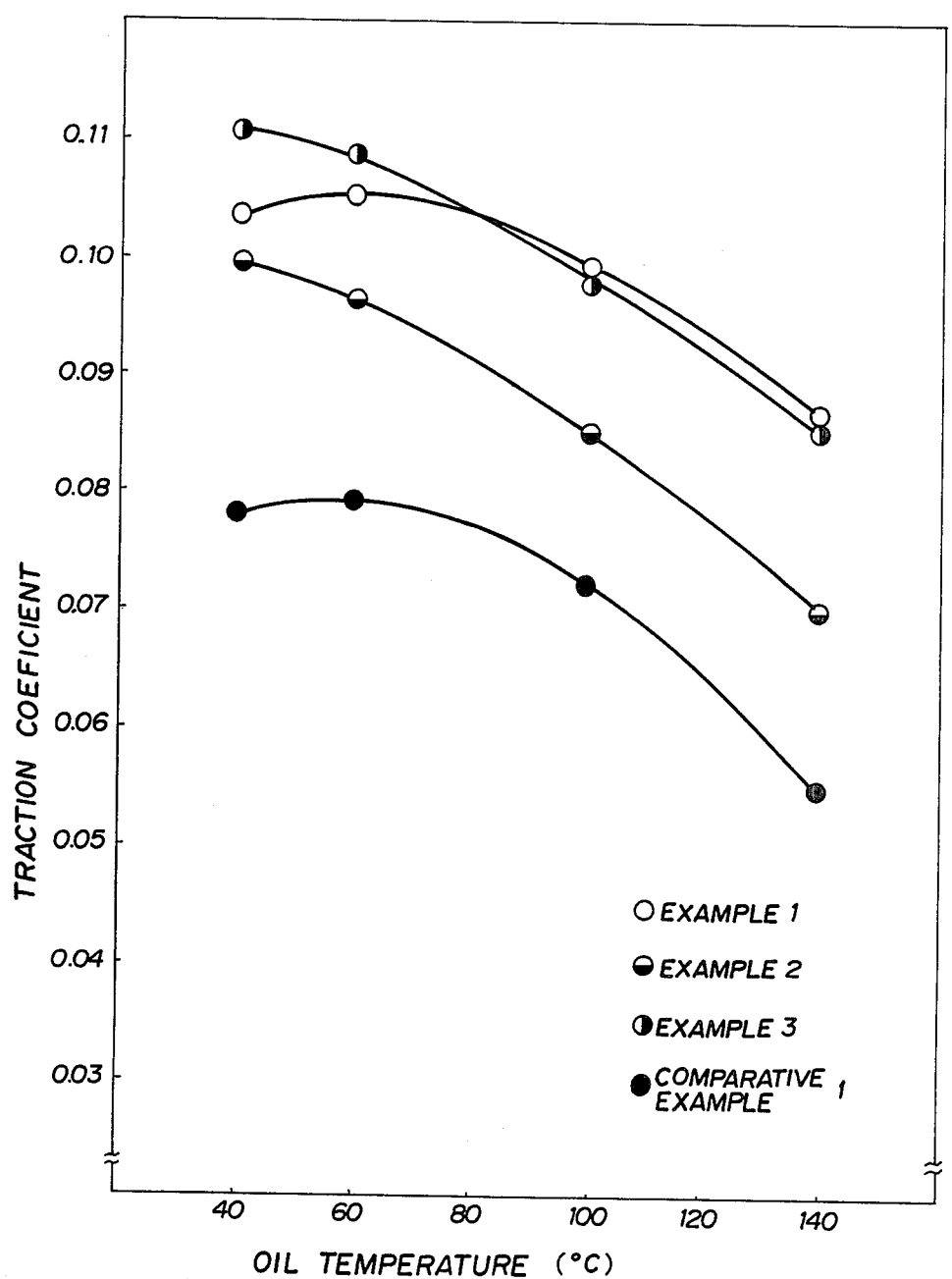
FIG. 4 is a graph which shows the relation between traction coefficient and oil bath temperature for the derivative.

The results are shown in FIG. 4.

EXAMPLE 2

(1) Preparation of fluorene derivative

A fluorene derivative was prepared in the same manner as in Example 1 (1) except that 223 g (1.03 mol) of 1,4-dibromobutane was used in place of 237 g (1.03 mol) of 1,5-dibromopentane. The resulting fluorene derivative had a melting point of 85°–87° C.

(2) Preparation of perhydrofluorene derivative

Perhydrospiro[cyclopentane-1,9'-fluorene] of 99% in purity was obtained in the same manner as in Example 1 (2) using the fluorene derivative obtained in (1) hereabove.

The results are shown in Table 1.

Figure 5:
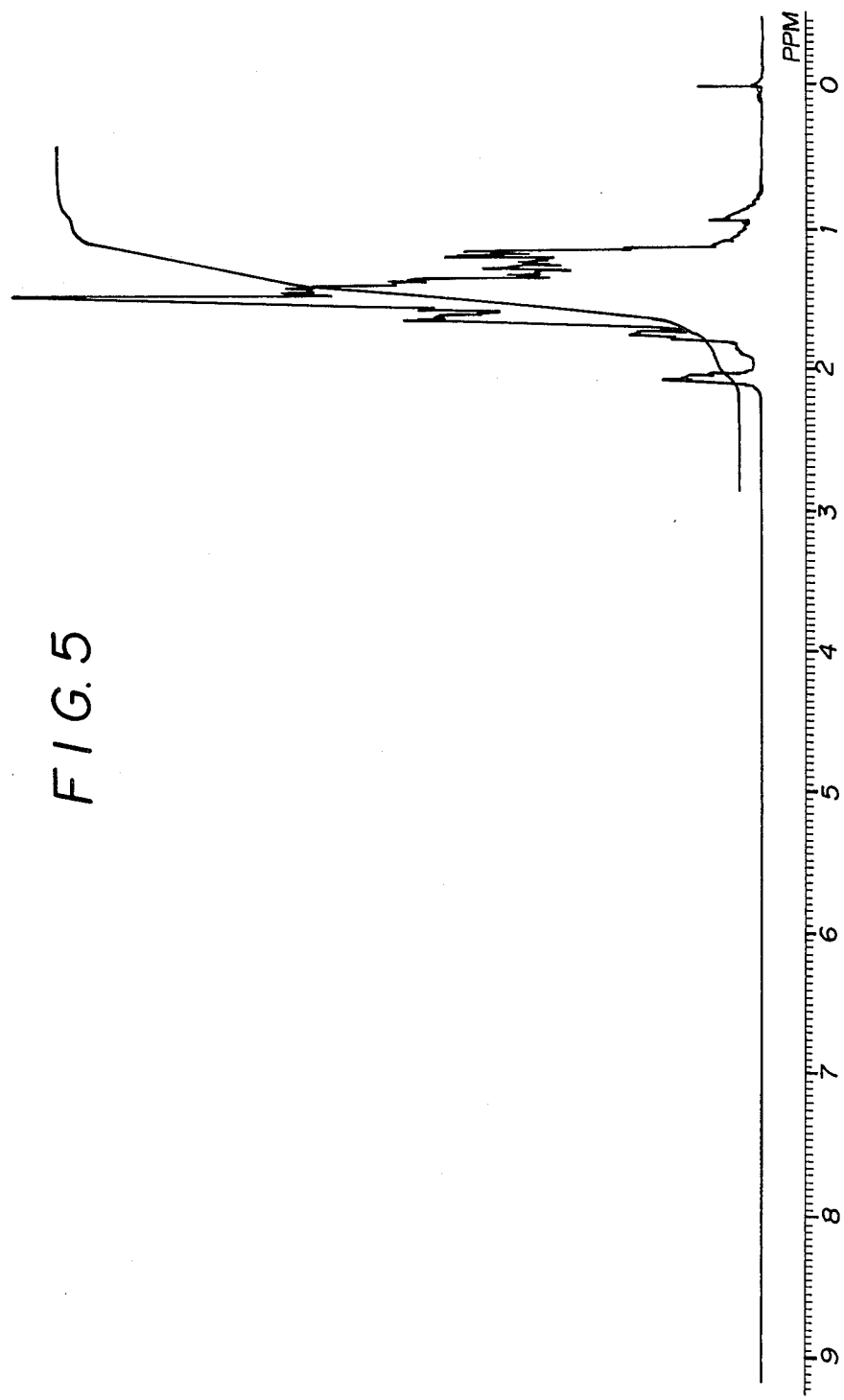
FIG. 5 is a spectral chart which shows the results of proton nuclear magnetic resonance spectral analysis of another example of the perhydrofluorene derivative of this invention.
Figure 6:
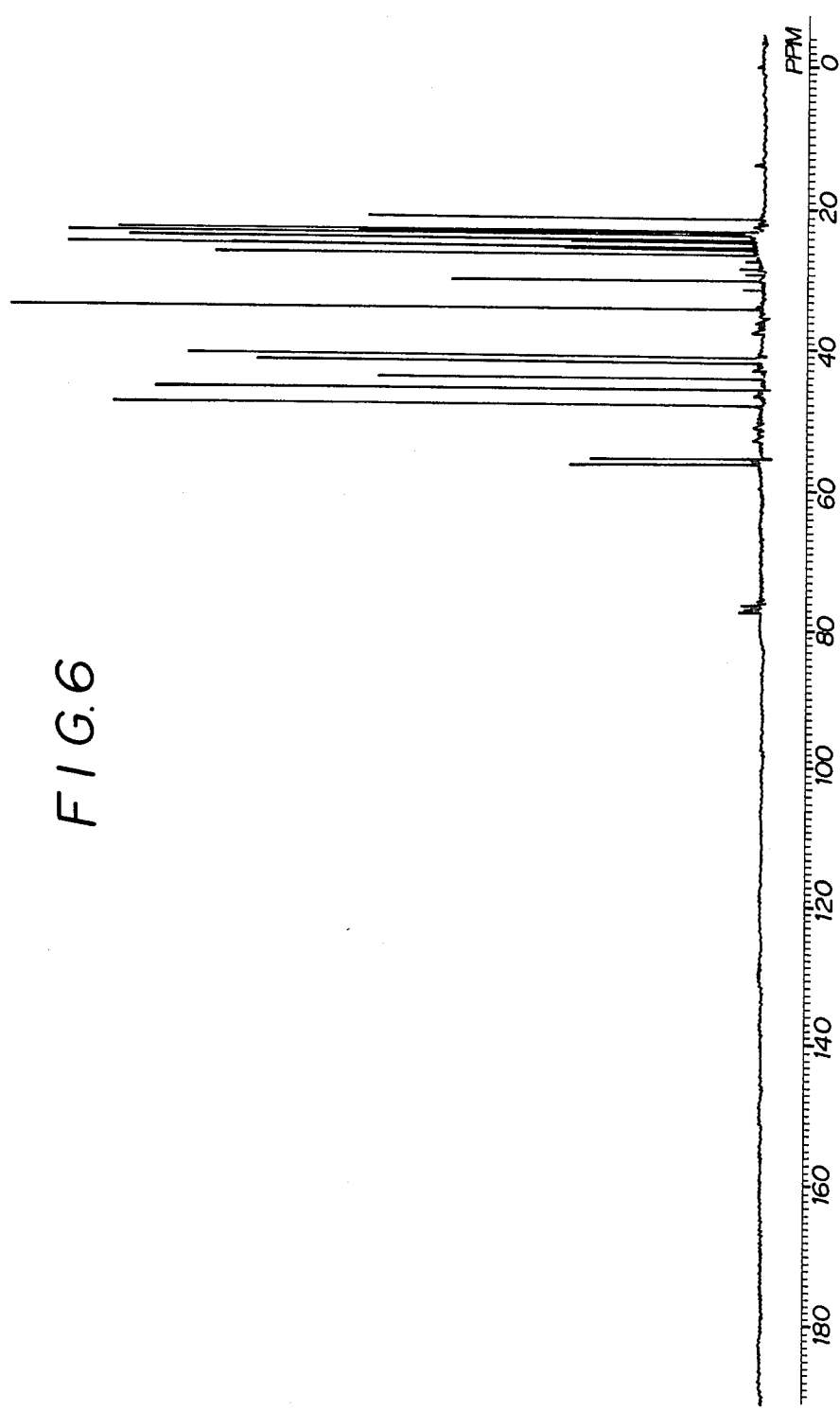
FIG. 6 is a spectral chart which shows the results of 13C nuclear magnetic resonance spectral analysis of the derivative.
Figure 7:
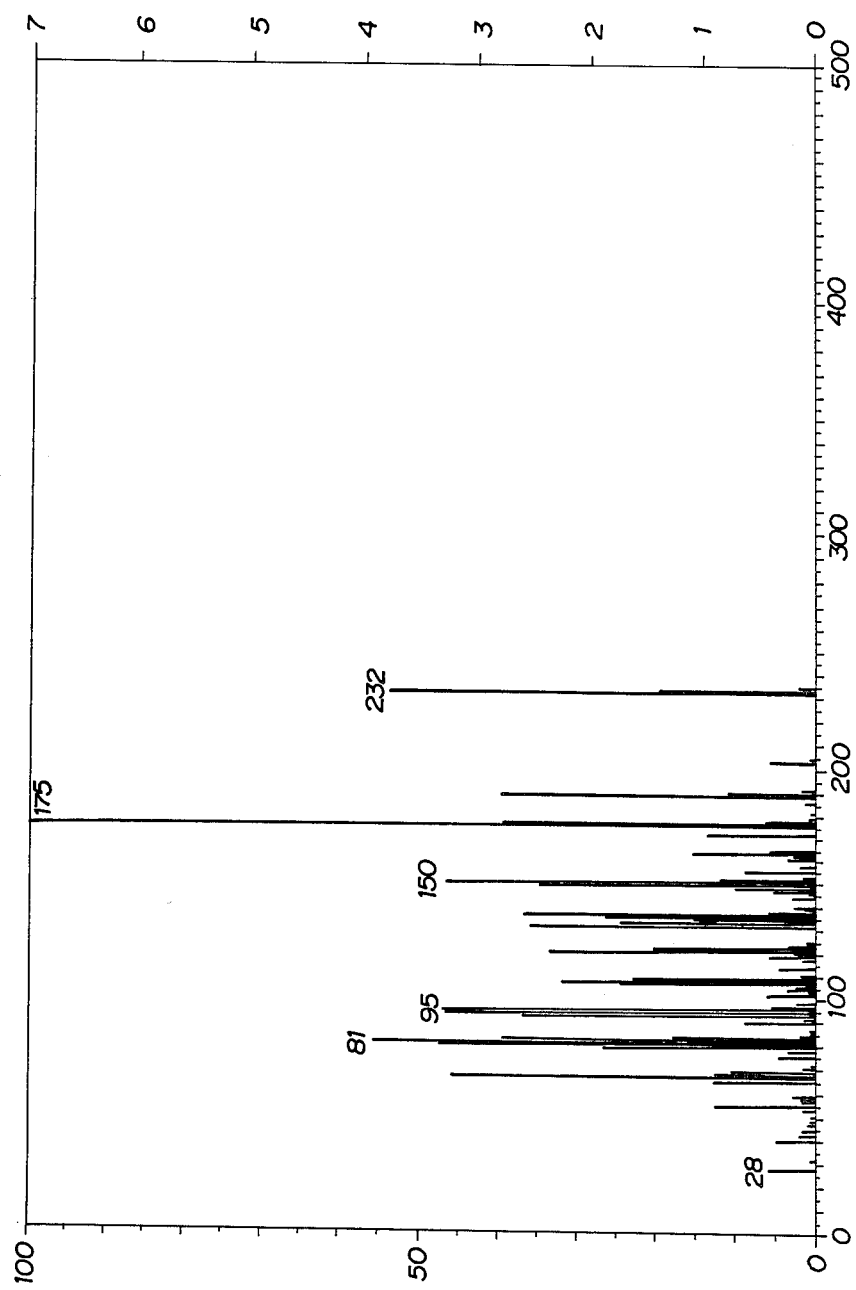
FIG. 7 is spectral chart which shows the results of mass spectral analysis of the derivative.

Results of proton nuclear magnetic resonance spectral analysis are shown in FIG. 5, those of $^{13}C$ nuclear magnetic resonance spectral analysis are shown in FIG. 6 and those of mass spectral analysis are shown in FIG. 7.

(3) Measurement of traction coefficient

Traction coefficient of the perhydrofluorene derivative obtained in the above (2) was measured in the same manner as in Example 1 (3).

The results are shown in FIG. 4.

EXAMPLE 3

(1) Preparation of fluorene derivative

A fluorene derivative was prepared in the same manner as in Example 1 (1) except that 371 g (1.03 mol) of o-xylylene dibromide was used in place of 237 g (1.03 mol) of 1,5-dibromopentane.

(2) Preparation of perhydrofluorene derivative

Perhydrospiro[fluorene-9,2'-indane] of 99% in purity was prepared in the same manner as in Example 1 (2) using the fluorene derivative obtained in (1) hereabove.

The results are shown in Table 1.

Figure 8:
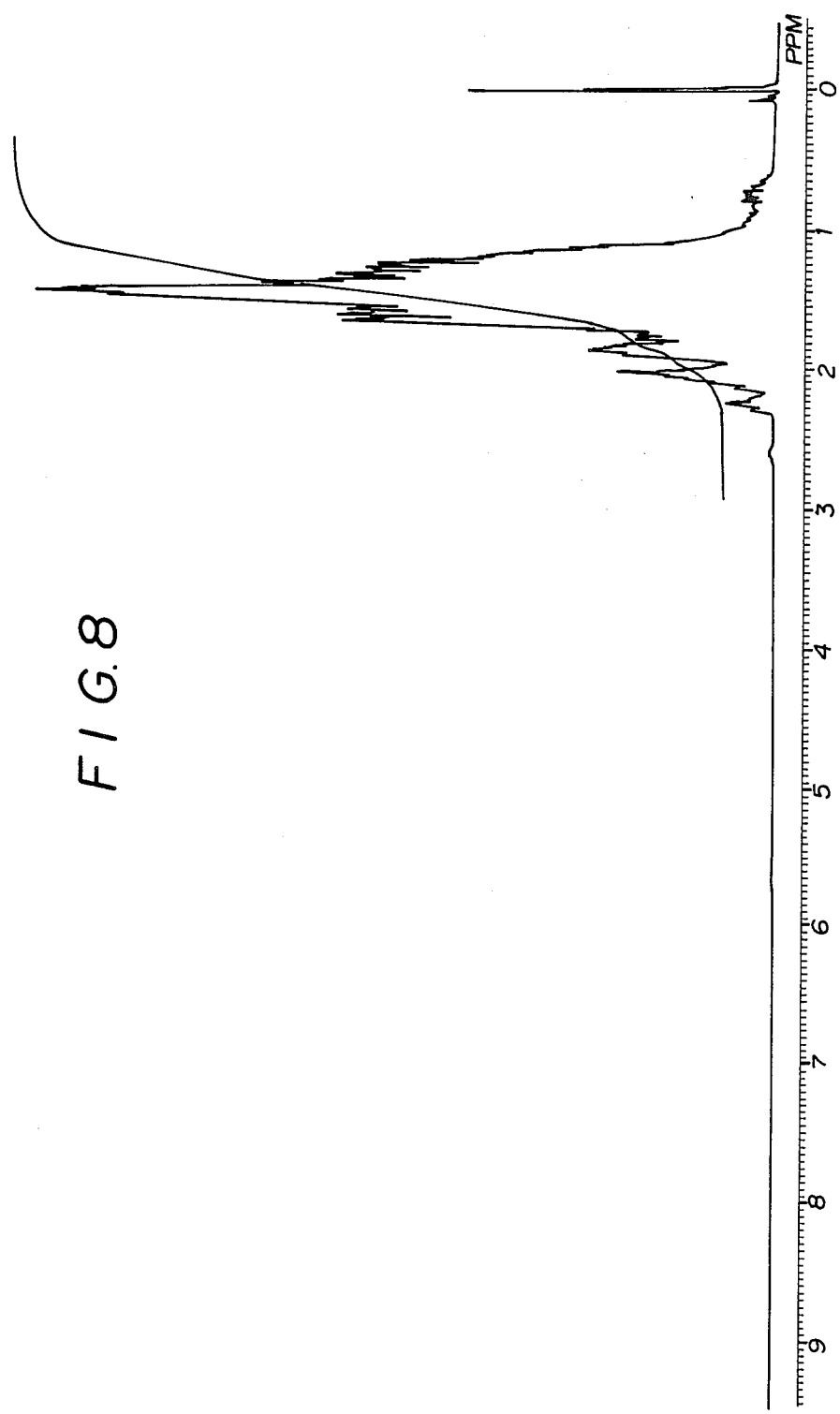
FIG. 8 is a spectral chart which shows the results of proton nuclear magnetic resonance spectral analysis of further another perhydrofluorene derivative of this invention.
Figure 9:
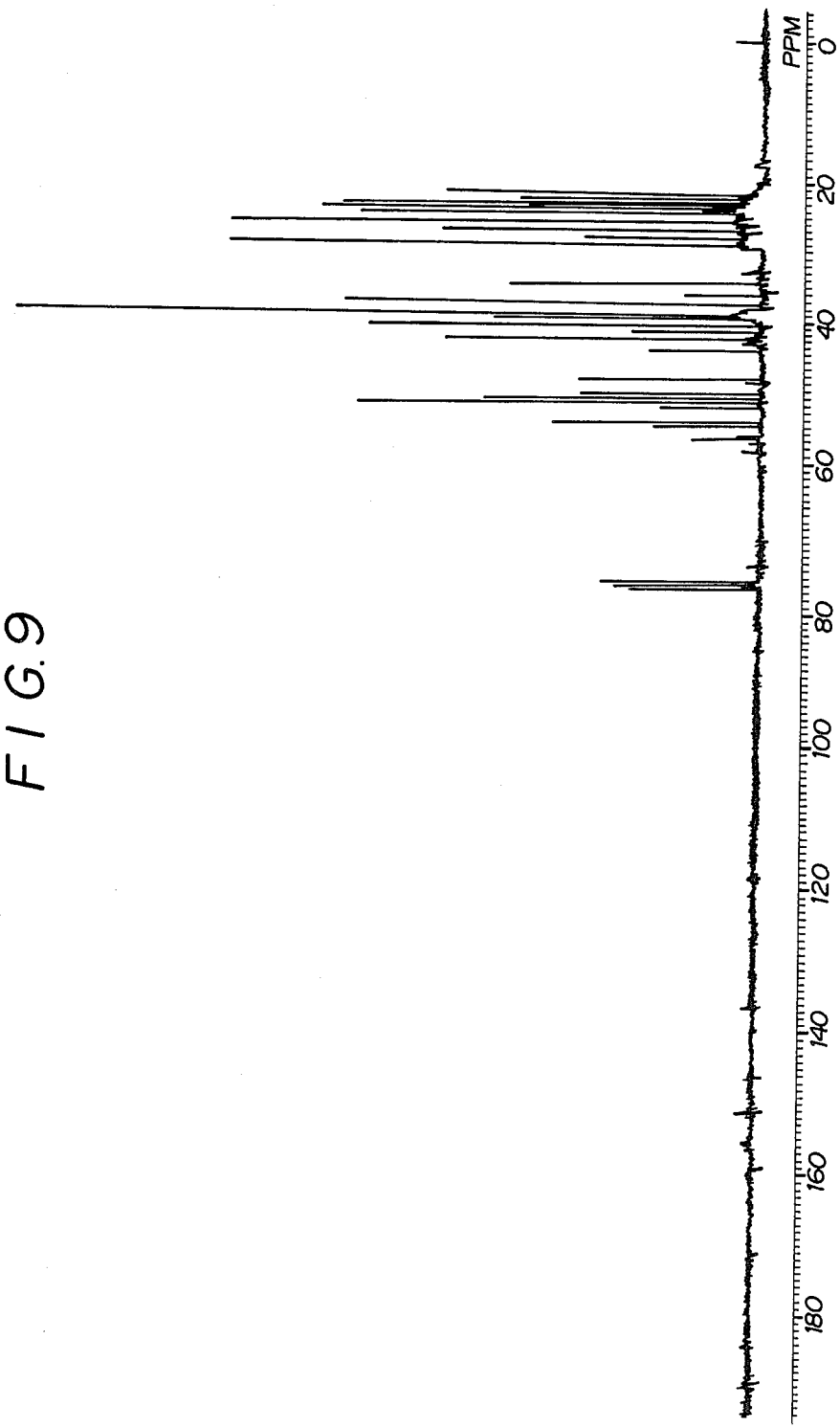
FIG. 9 is a spectral chart which shows the results of 13C nuclear magnetic resonance spectral analysis of the derivative.
Figure 10:
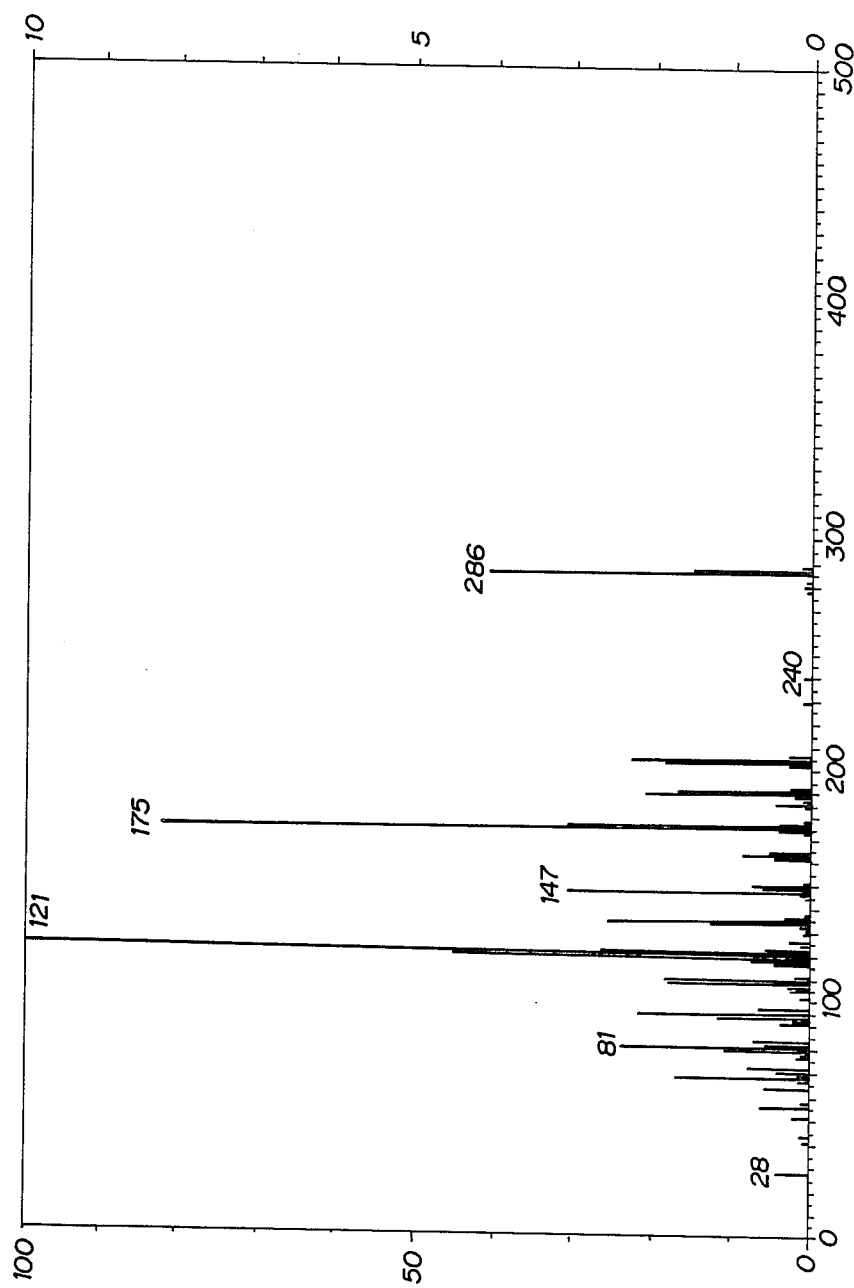
FIG. 10 is a spectral chart which shows the results of mass spectral analysis of the derivative.

The results of proton nuclear magnetic resonance spectral analysis are shown in FIG. 8, those of $^{13}C$ nuclear magnetic resonance spectral analysis are shown in FIG. 9 and those of mass spectral analysis are shown in FIG. 10.

(3) Measurement of traction coefficient

Traction coefficient of the perhydrofluorene derivative obtained in the above (2) was measured in the same manner as in Example 1 (3).

The results are shown in FIG. 4.

COMPARATIVE EXAMPLE 1

In a four necked flask of 5 liters provided with a dropping funnel with bypass, a thermometer and a stirrer were charged 540 g of fluorene, 40 g of anhydrous aluminum chloride and 2.5 liters of carbon tetrachloride. With stirring, thereto was added dropwise 320 g of benzyl chloride over a period of 8 hours at room temperature and after completion of the addition, stirring was effected for further 30 minutes. Aluminum chloride was deactivated with addition of water and then the oily layer was washed with a saturated aqueous sodium chloride solution and a 1N aqueous sodium hydroxide solution and dried over anhydrous magnesium sulfate. The drying agent was removed by filtration and then carbon tetrachloride and unreacted fluorene were distilled off by rotary evaporator. Then, the residue was distilled under reduced pressure to obtain 250 g of a fraction having a boiling point of 166°–178° C./0.12 mmHg. Analysis of this fraction showed that this was mainly composed of benzylfluorene having the substituent in benzene nucleous.

Then, 250 g of this fraction and 25 g of 5% ruthenium-active carbon catalyst (manufactured by Japan Engelhard Co.) were charged in an autoclave of 1 liter and hydrogenation was effected at a hydrogen pressure of 100 kg/cm²G and at a reaction temperature of 200° C. for 4 hours. The catalyst was removed by filtration to obtain 240 g of a fluid mainly composed of (cyclohexylmethyl)-perhydrofluorene.

The results are shown in Table 1.

Prperties of this fluid were kinematic viscosity: 79.51 cSt (@ 40° C.) and 6.425 cSt (@ 100° C.); specific gravity: 0.9646 (15/4° C.); pour point: −20° C.; refractive index: 1.5138 $n^{20}D$.

Traction coefficients of this fluid at from 40° C. to 140° C. were measured and the results are shown in FIG. 4.

As is clear from the above, the compound of this invention has very high traction coefficient among those compounds which have the same perhydrofluorene skeleton.

TABLE 1

| | | Example 1 | Example 2 | Example 3 | Comparative Example 1 |
|---|---|---|---|---|---|
| Kinematic viscosity (cst) | 40° C. | 49.91 | 18.10 | 1333 | 79.51 |
| | 100° C. | 5.062 | 3.567 | 14.60 | 6.425 |
| Specific gravity | | 1.005 | 0.9962 | 1.0296 | 0.9646 |
| Viscosity index | | −70 | 58 | −754 | −60 |
| Pour point (°C.) | | −17.5 | −35 or less | +5.0 | −20.0 |
| Refractive index | | 1.5288 | 1.5236 | 1.5439 | 1.5138 |

Viscosity index: in accordance with JIS K 2284
Pour point: in accordance with JIS K 2269

What is claimed is:

1. A perhydrofluorene derivative which is represented by the formula [1]:

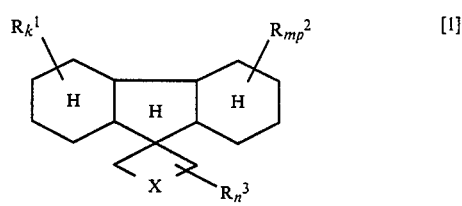

wherein $R^1$, $R^2$ and $R^3$ each represents a hydrogen atom or an alkyl group of 1-4 carbon atoms; X represents $(CH_2)_p$ or

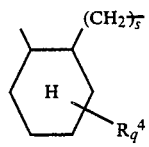

wherein $R^4$ represents a hydrogen atom or an alkyl group of 1–4 carbon atoms, p represents a real number of 2–6, q represents a real number of 1–4 and s represents 1 or 0; and k, m and n each represents a real number of 1–4.

2. A perhydrofluorene derivative according to claim 1 wherein in the formula 1, $R^1$, $R^2$ and $R^3$ each represents a hydrogen atom or a methyl group, X represents $(CH_2)_3$, $(CH_2)_4$ or

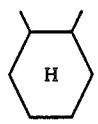

and k, m and n each represents a real number of 1–4.

3. A perhydrofluorene derivative according to claim 1 wherein in the formula 1, $R^1$, $R^2$ and $R^3$ each represents a hydrogen atom, X represents $(CH_2)_3$, $(CH_2)_4$ or

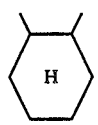

and k, m and n each represents 4.

4. A fluid for traction drive which contains a perhydrofluorene derivative represented by the formula [1]:

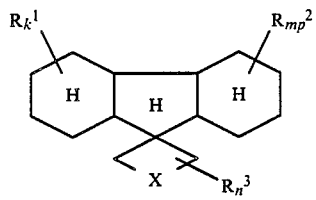

wherein $R^1$, $R^2$ and $R^3$ each represents a hydrogen atom or an alkyl group of 1–4 carbon atoms; X represents $(CH_2)_p$ or

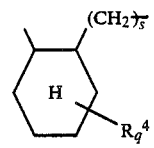

wherein $R^4$ represents a hydrogen atom or an alkyl group of 1–4 carbon atoms, p represents a real number of 2–6, q represents a real number of 1–4 and s represents 1 or 0; and k, m and n each represents a real number of 1–4.

5. A fluid for traction drive according to claim 4 wherein in the formula 1, $R^1$, $R^2$ and $R^3$ each represents a hydrogen atom or a methyl group, X represents $(CH_2)_3$, $(CH_2)_4$ or

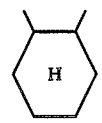

and k, m and n each represents a real number of 1–4.

6. A fluid for traction drive according to claim 4 wherein in the formula 1, $R^1$, $R^2$ and $R^3$ each represents a hydrogen atom, X represents $(CH_2)_3$, $(CH_2)_4$ or

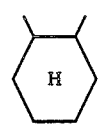

and k, m and n each represents 4.

* * * * *